(12) United States Patent
Ni et al.

(10) Patent No.: US 8,553,967 B2
(45) Date of Patent: Oct. 8, 2013

(54) SYSTEM AND METHOD FOR A DIGITAL X-RAY RADIOGRAPHIC TOMOSYNTHESIS USER INTERFACE

(75) Inventors: Xianfeng Ni, Sussex, WI (US); John Michael Sabol, Sussex, WI (US); Renuka Uppaluri, Pewaukee, WI (US); Kadri Nizar Jabri, Waukesha, WI (US); Tammy Michael Merisotis, Murrells Inlet, SC (US)

(73) Assignee: General Electric Company, Schenectady, NY (US)

( * ) Notice: Subject to any disclaimer, the term of this patent is extended or adjusted under 35 U.S.C. 154(b) by 1295 days.

(21) Appl. No.: 11/852,470

(22) Filed: Sep. 10, 2007

(65) Prior Publication Data

US 2009/0003679 A1    Jan. 1, 2009

Related U.S. Application Data

(60) Provisional application No. 60/947,390, filed on Jun. 29, 2007.

(51) Int. Cl.
*G06K 9/00* (2006.01)
*A61B 5/05* (2006.01)

(52) U.S. Cl.
USPC .............................. 382/132; 382/131; 600/425

(58) Field of Classification Search
USPC .................... 382/128–132; 378/26; 600/425
See application file for complete search history.

(56) References Cited

U.S. PATENT DOCUMENTS

| 4,903,204 | A | 2/1990 | Dobbins |
| 6,196,715 | B1 | 3/2001 | Nambu et al. |
| 6,529,575 | B1 | 3/2003 | Heish |
| 6,718,055 | B1* | 4/2004 | Suri ............................... 382/128 |
| 7,123,684 | B2 | 10/2006 | Jing et al. |
| 7,250,949 | B2 | 7/2007 | Claus et al. |
| 2002/0080921 | A1 | 6/2002 | Smith et al. |
| 2002/0141532 | A1 | 10/2002 | Koppe et al. |
| 2004/0165758 | A1* | 8/2004 | Furudate et al. ............... 382/132 |
| 2005/0002550 | A1* | 1/2005 | Jabri et al. ..................... 382/131 |

(Continued)

FOREIGN PATENT DOCUMENTS

| JP | 2001-149366 A | 6/2001 |
| JP | 2002-216108 A | 8/2002 |

(Continued)

OTHER PUBLICATIONS

Li et al., The impact of acquisition angular range on the z-resolution of radiographic tomosynthesis, Jun. 2004, International Congress Series, vol. 1268, pp. 13-18, Proceedings of the 18th International Congress and Exposition—CARS 2004—Computer Assisted Radiography and Surgery.

(Continued)

*Primary Examiner* — Amara Abdi
(74) *Attorney, Agent, or Firm* — William Baxter; Patrick J. Kim

(57) ABSTRACT

A system and method for an improved digital X-ray radiographic tomosynthesis user interface and workflow. The system comprising a user interface providing a tomosynthesis reconstruction preference edit tool; a dose preference edit tool; a scout acquisition edit tool; a tomosynthesis acquisition edit tool; a retrospective reconstruction image processing edit tool; a slice image change auto forward edit tool; and an image annotation propogation edit tool.

17 Claims, 14 Drawing Sheets

(56) References Cited

U.S. PATENT DOCUMENTS

| | | | |
|---|---|---|---|
| 2005/0110748 A1 | 5/2005 | Boeing et al. | |
| 2005/0267348 A1* | 12/2005 | Wollenweber et al. | 600/407 |
| 2006/0018435 A1* | 1/2006 | Toth et al. | 378/165 |
| 2006/0029285 A1* | 2/2006 | Hein et al. | 382/260 |
| 2006/0098855 A1 | 5/2006 | Gkanatsios et al. | |
| 2006/0274925 A1* | 12/2006 | West et al. | 382/131 |
| 2006/0291614 A1* | 12/2006 | Horiuchi et al. | 378/4 |
| 2007/0101295 A1 | 5/2007 | Ding et al. | |
| 2007/0276220 A1* | 11/2007 | Harvey et al. | 600/410 |
| 2009/0171203 A1* | 7/2009 | Avital et al. | 600/439 |

FOREIGN PATENT DOCUMENTS

| | | |
|---|---|---|
| JP | 2003-070778 A | 3/2003 |
| JP | 2005-124975 A | 5/2005 |
| JP | 2006-142016 A | 6/2006 |
| JP | 2007-020813 A | 2/2007 |
| JP | 2011-126697 A | 6/2011 |
| WO | WO2004049949 A1 | 6/2004 |

OTHER PUBLICATIONS

Harder, Ben. (Dec. 10, 2005). "3-D Vision: New technique could improve breast cancer screening, diagnosis." Science News, vol. 168, (No. 24), p. 371.

Dobbins JT, Webber RL, Hames SM. "Tomosynthesis for improved pulmonary nodule detection (abstr.)". Radiology 1998; 209(P):280.

Hu, Hui et al. "The effect of helical pitch and beam collimation on the lesion contrast and slice profile in helical CT imaging", Medical Phys. 23, pp. 1943-1954, 1996.

Japanese Office Action issued on co-pending application No. JP2008-161137 dated Oct. 9, 2012, 3 pages.

Japanese Office Action issued on co-pending application No. JP2008-161137 dated Jan. 29, 2013, 3 pages.

* cited by examiner

FIG. 9

TOMO, VOLUME...
NEW PATIENTID

HAND_VolumeRAD
PA
LAT

HAND_VolumeRAD - PA(VolumeRAD Acquisition)    TOTAL DOSE: 0.05 mGy
                                              TOTAL DAP: 0.11 dGycm^2

PATIENT SIZE          RECEPTOR:
MEDIUM ADULT

RESET TECHNIQUE:                              CURRENT: GRID  SID
                                                      OUT  110.7      FIXED
                                              RECOMMENDED: OUT  100
                                              # OF SLICES: 29  ACQUISTIONS: 40  TOTAL TIME: 8 sec 50              125.0
                        kV              mA FOCAL SPOT:
Cu FILTER: 0.0          0.25            2.0
PATIENT SIDE:           mAs             mSec
RIGHT
PATIENT POSITION:       PERFORM AUTO - POSITIONING TO MOVE
DIGITS TO HEAD          THE TUBE INTO INITIAL POSITION FOR
                        VolumeRAD AQUISITION.

RETAKE SCOUT — 910

SELECT PROTOCOLS
☐ AUTO SEND
SUSPEND  CLOSE
DISCONTINUE             MESSAGE LOG  QAP  WARM TUBE    iLinq

HEAT UNITS REMAINING: 97%

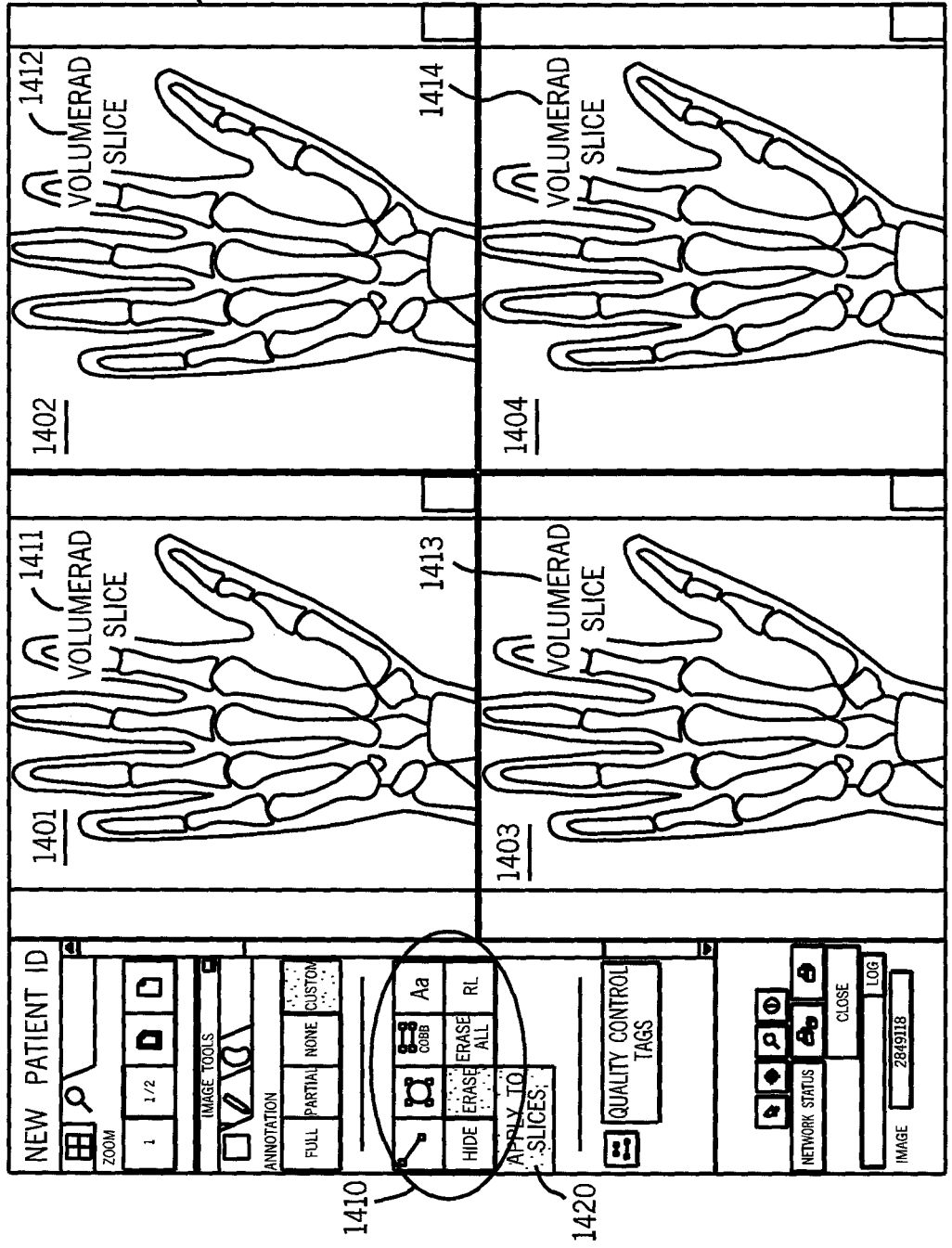

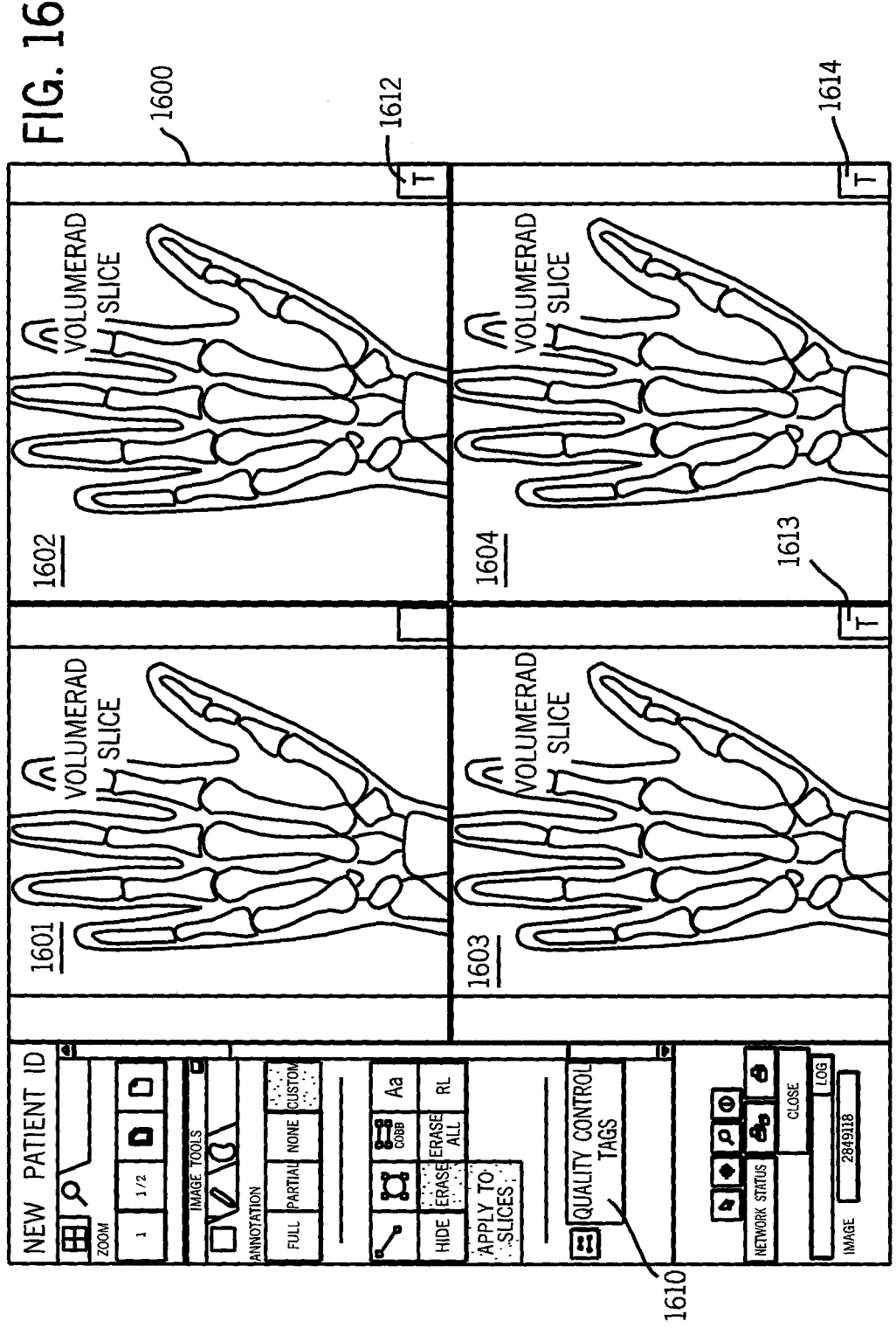

SYSTEM AND METHOD FOR A DIGITAL X-RAY RADIOGRAPHIC TOMOSYNTHESIS USER INTERFACE

CROSS-REFERENCE TO RELATED APPLICATIONS

This application is based on and claims the benefit of U.S. Provisional Patent Application No. 60/947,390, filed Jun. 29, 2007, the disclosure of which is incorporated herein by reference.

BACKGROUND OF THE INVENTION

This disclosure relates generally to X-ray systems and methods, and more particularly to a system and method for an improved digital X-ray radiographic tomosynthesis user interface and workflow.

In a conventional digital X-ray radiographic system, an X-ray beam is generated from a stationary X-ray source and projected through a patient to be imaged onto a stationary X-ray detector. A typical patient exam on a conventional digital X-ray radiographic system consists of one or several single exposure acquisitions each of a different projection of the patient's anatomy. Thus, the number of images for an exam may be quite limited.

In a digital X-ray radiographic tomosynthesis system, an X-ray beam is generated from an X-ray source moving within a limited angular range and projected through a patient to be imaged onto a stationary X-ray detector. Digital tomosynthesis is a limited angle imaging technique, which allows the reconstruction of three-dimensional (3D) images from a series of two-dimensional (2D) projection images of a patient. It enables 3D imaging of a patient to be generated from a series of 2D images. A series of 2D projection images of a patient are obtained, each at a different projection angle, and a 3D image is generated from the series of 2D projection images.

A digital tomosynthesis acquisition involves a series of low dose exposures during a single sweep of an X-ray source moving within a limited angular range of a stationary detector. 3D image data is generated in the form of a number of slices through the patient, each parallel to the detector plane. After the digital tomosynthesis acquisition, the digital tomosynthesis system reconstructs a number of planes called slices parallel to the detector. These slices show anatomical structures at different depths. The digital X-ray radiographic tomosynthesis system removes overlapping and overlaying structures and enhances the conspicuity (clarity and brightness) of structures in the different slices.

A digital X-ray radiographic tomosynthesis acquisition is quite different from a conventional digital X-ray radiographic acquisition, having a different configuration, different workflow, using different techniques, and providing different images, etc. Due to the complexity of a digital X-ray radiographic tomosynthesis acquisition, and the number of parameters that need to be specified, it is desirable to provide a simple user-friendly user interface that will allow a user to select the desired reconstruction, dose, and acquisition parameters based on the clinical requirements of each exam.

Therefore, there is a need for a digital X-ray radiographic tomosynthesis system having an improved user interface with a set of user-friendly interfaces that can assist users in selecting preferences, desired dose and reconstruction settings, without needing to understand or become involved in the complexities of the tomosynthesis technique.

BRIEF DESCRIPTION OF THE INVENTION

In an embodiment, a tomosynthesis system comprising a user interface providing a tomosynthesis preference edit tool enabling a user to customize slice reconstruction parameters for a specific anatomical view and patient size.

In an embodiment, a tomosynthesis system comprising a user interface providing a scout acquisition edit tool enabling a user to accept or edit scout acquisition parameters.

In an embodiment, a tomosynthesis system comprising a user interface providing a tomosynthesis acquisition edit tool enabling a user to accept or edit tomosynthesis acquisition parameters, wherein the tomosynthesis acquisition edit tool enables a user to retake a scout acquisition.

In an embodiment, a tomosynthesis system comprising a user interface providing a tomosynthesis preference edit tool enabling a user to customize dose parameters for a specific anatomical view and patient size.

In an embodiment, a tomosynthesis system comprising a user interface providing a tomosynthesis preference edit tool enabling a user to customize slice reconstruction parameters and dose parameters for a specific anatomical view and patient size.

Various other features, objects, and advantages will be made apparent to those skilled in the art from the accompanying drawings and detailed description thereof.

BRIEF DESCRIPTION OF THE DRAWINGS

FIG. 9 is a schematic representation of an exemplary embodiment of a user interface tomosynthesis acquisition edit tool illustrating a "Retake Scout" function;

FIG. 10 is a schematic representation of an exemplary embodiment of a user interface tomosynthesis acquisition edit tool illustrating an "Edit Recon" (edit reconstruction) function;

FIG. 14 is a schematic representation of an exemplary embodiment of a user interface "Image Annotation Propagation" tool;

FIG. 16 is a schematic representation of an exemplary embodiment of a user interface "Image Viewer Show Slices Tagged" tool.

DETAILED DESCRIPTION OF THE INVENTION

In the following detailed description, reference is made to the accompanying drawings that form a part hereof, and in which is shown by way of illustration specific exemplary embodiments which may be practiced. These exemplary embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
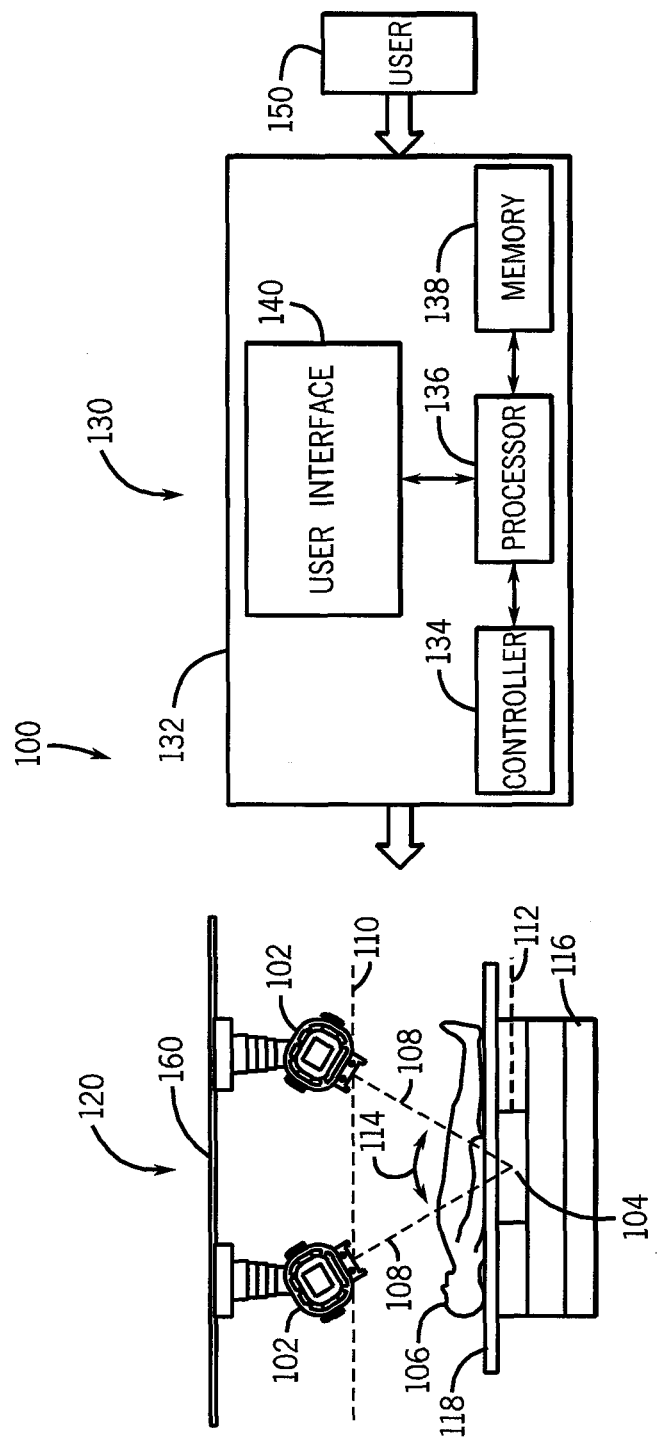
FIG. 1 is a schematic diagram of an exemplary embodiment of a digital X-ray radiographic tomosynthesis system having a table configuration.
Figure 2:
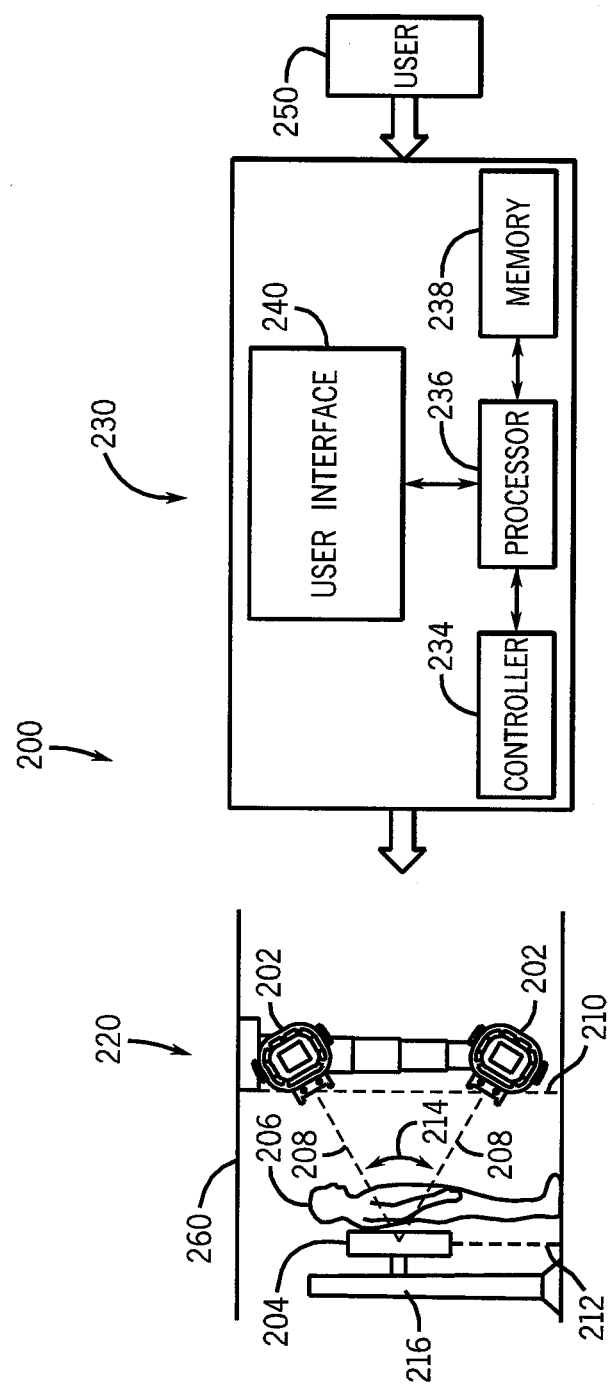
FIG. 2 is a schematic diagram of an exemplary embodiment of a digital X-ray radiographic tomosynthesis system having a wallstand configuration.

Referring now to the drawings, FIGS. 1 and 2 illustrate exemplary embodiments of a digital X-ray radiographic tomosynthesis system 100, 200. FIG. 1 illustrates a table acquisition configuration having an X-ray source 102 attached to a structure 160 and an X-ray detector 104 positioned within a table 116 under a table top 118, while FIG. 2 illustrates a wallstand configuration having an X-ray source 202 attached to a structure 260 and an X-ray detector 204 attached to a wallstand 216. The digital X-ray radiographic tomosynthesis radiography system 100, 200 includes an X-ray source 102, 202, which subject a patient under examination 106, 206 to radiation in the form of an X-ray beam 108, 208. The X-ray beam 108, 208 is emitted by the X-ray source 102, 202 and impinges on the patient 106, 206 under examination. A portion of radiation from the X-ray beam 108, 208 passes through or around the patient and impacts the detector 104, 204.

In an exemplary embodiment, the X-ray source 102, 202 may be an X-ray tube, and the patient under examination 106, 206 may be a human patient, an animal patient, a test phantom, and/or other inanimate object under examination.

The patient under examination 106, 206 is placed between the X-ray source 102, 202 and the detector 104, 204. During tomosynthesis acquisition, the X-ray source 102, 202 travels along the plane 110, 210 illustrated in FIGS. 1 and 2, and rotates in synchrony such that the X-ray beam 108, 208 is always pointed at the detector 104, 204 during the acquisition. As mentioned above, the X-ray source 102, 202 is typically moved along the single plane 110, 210 parallel to the plane 112, 212 of the detector 104, 204, although it may be moved outside of a single plane, which is substantially parallel to the detector 104, 204. The detector 104, 204 is maintained at a stationary position as radiographs are acquired. A plurality of discrete projection radiographs of the patient 106, 206 are acquired by the detector 104, 204 at discrete locations along the path 110, 112 of the X-ray source 102, 202. After acquiring projection image data from the projection radiographs, application software may be to reconstruct slice images.

The digital X-ray radiographic tomosynthesis imaging process includes a series of low dose exposures during a single sweep of the X-ray source 102, 202 moving within a limited angular range 114, 214 (sweep angle) by arc rotation or linear translation of the X-ray source 102, 202 and focused toward the stationary detector 104, 204. The X-ray source 102, 202 delivers multiple exposures during the single sweep from multiple projection angles. The sweep angle 114, 214 is the angle from the first projection exposure to the final projection exposure. The sweep angle 114, 214 is typically within a range from 20 to 60 degrees.

In an exemplary embodiment, the detector 104, 204 may comprise a plurality of detector elements, generally corresponding to pixels, which sense the intensity of X-rays that pass through and around patients and produce electrical signals that represent the intensity of the incident X-ray beam at each detector element. These electrical signals are acquired and processed to reconstruct a 3D volumetric image of the patient's anatomy. Depending upon the X-ray attenuation and absorption of intervening structures, the intensity of the X-rays impacting each detector element will vary.

FIGS. 1 and 2 further schematically illustrate a computer workstation 130, 230 coupled to a digital tomosynthesis imaging system 120, 220 of the digital X-ray radiographic tomosynthesis system 100, 200 providing a user interface 140, 240 for selecting at least one reconstruction, dose, and/or acquisition parameter for the digital X-ray radiographic tomosynthesis acquisition as described herein.

The digital tomosynthesis imaging system 120, 220 may be used for acquiring and processing projection image data and reconstructing a volumetric image or three-dimensional (3D) image representative of an imaged patient. The digital tomosynthesis imaging system 120, 220 is designed to acquire projection image data and to process the image data for viewing and analysis.

The computer workstation 130, 230 includes at least one computer 132, 232 with a controller 134, 234, a processor 136, 236, memory 138, 238, and a user interface 140, 240. The processor 136, 236 may be coupled to the controller 134, 234, the memory 138, 238, and the user interface 140, 240. A user 150, 250 interacts with the computer workstation 130, 230 for controlling operation of the digital X-ray radiographic tomosynthesis system 100, 200. In an exemplary embodiment, the memory 138, 238 may be in the form of memory devices, memory boards, data storage devices, or any other storage devices known in the art.

The digital tomosynthesis imaging system 120, 220 is controlled by the controller 134, 234, which may furnish both power and control signals for digital tomosynthesis examination sequences, including positioning of the X-ray source relative to the patient and the detector. The controller 134, 234 may command acquisition of signals generated in the detector. The controller 134, 234 may also execute various signal processing and filtering functions, such as for initial adjustment of dynamic ranges, interleaving of digital image data, and so forth. In general, the controller 134, 234 commands operation of the digital tomosynthesis imaging system 120, 220 to execute examination protocols and to process acquired data. In an exemplary embodiment, the controller 134, 234 receives instructions from the computer 132, 232. In an exemplary embodiment, the controller 134, 234 may be part of the digital tomosynthesis imaging system 120, 220, instead of the computer workstation 130, 230.

In an exemplary embodiment, the computer 132, 232 includes or is coupled to the user interface 140, 240 for interaction by the user 150, 250 for selecting and/or changing clinically relevant parameters, such as dose, slice placement (reconstruction settings), and acquisition parameters. In an exemplary embodiment, operation of the digital X-ray radiographic tomosynthesis system 100, 200 is implemented through the use of software programs or algorithms downloaded on or integrated within the computer 132, 232.

In an exemplary embodiment, the user interface 140, 240 is a visual interface that may be configured to include a plurality of pre-defined tools, which will allow a user 150, 250 to view, select and edit reconstruction parameters (settings); view and select dose parameters; and view, select and edit tomosynthesis acquisition parameters. The plurality of pre-defined tools may include a tomosynthesis preference edit tool, a "Scout" acquisition edit tool, a tomosynthesis acquisition edit tool, and a plurality of slice image processing edit tools. The user interface 140, 240 also allows the user 150, 250 to view the reconstructed images.

In an exemplary embodiment, the user interface 140, 240 may include at least one input device for inputting and/or selecting information on the plurality of pre-defined tools displayed on the display of the user interface 140, 240. In an exemplary embodiment, the at least one input device may be in the form of a touch screen display, a mouse, a keyboard, at least one push button, or any other input device known in the art.

Figure 3:
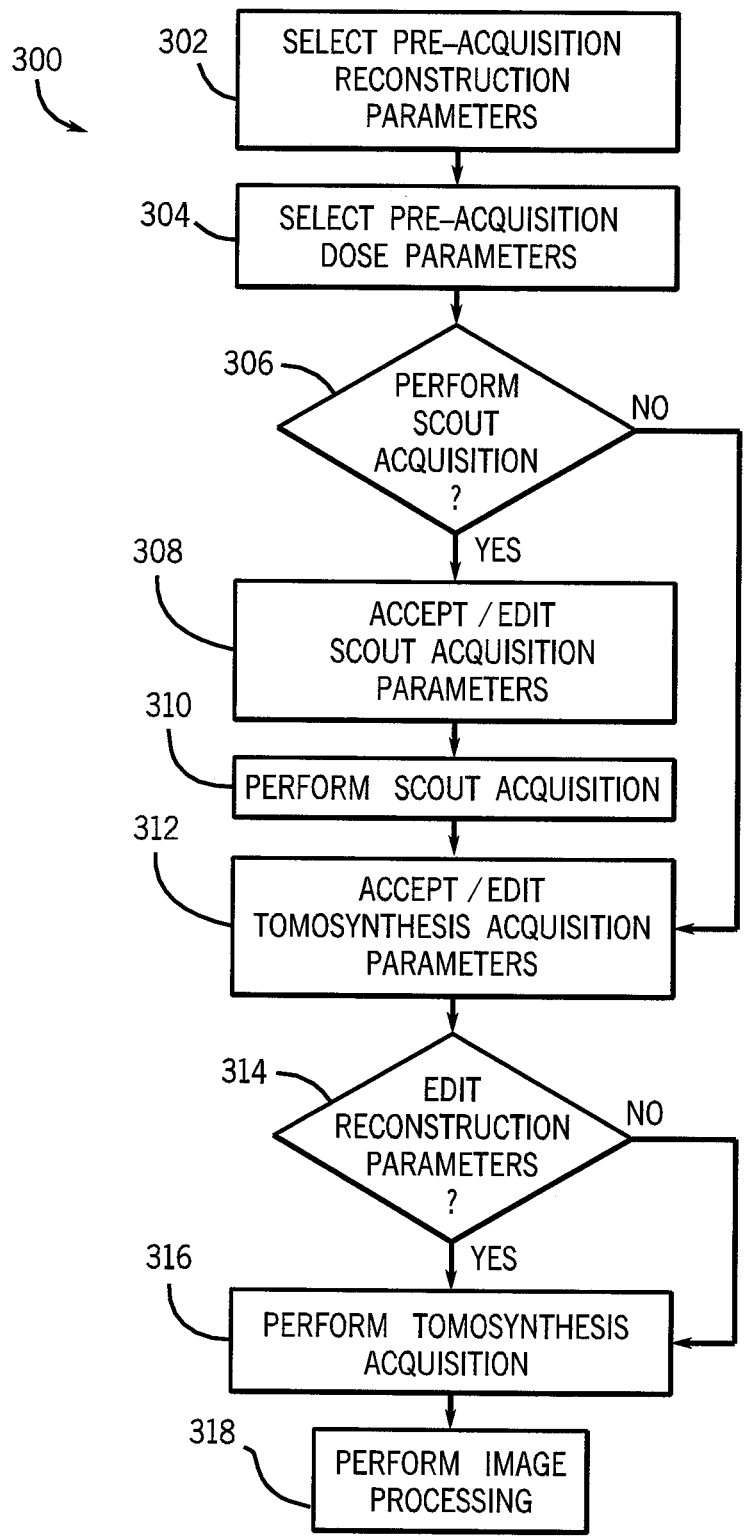
FIG. 3 is a flow diagram of an exemplary embodiment of a digital X-ray radiographic tomosynthesis system workflow method.

FIG. 3 is a flow diagram of an exemplary embodiment of a digital X-ray radiographic tomosynthesis system workflow method 300. This method 300 includes selecting pre-acquisition reconstruction parameters prior to the start of an X-ray exposure 302. The method 300 also includes selecting pre-acquisition dose parameters prior to the start of an X-ray exposure 304. Prior to the start of a tomosynthesis acquisition, the user is given the opportunity to perform a "Scout" acquisition to obtain an optimal tomosynthesis exam 306. If the user elects to perform a "Scout" acquisition, the user is given the ability to accept or edit default "Scout" acquisition parameters 308, prior to performing the "Scout" acquisition 310. If the user elects not to perform a "Scout" acquisition, the user is given the ability to accept or edit default tomosynthesis acquisition parameters 312, prior to performing a tomosynthesis acquisition 316. After performing the "Scout" acquisition 310, the user is given the ability to accept or edit default tomosynthesis acquisition parameters 312, prior to performing the tomosynthesis acquisition 316. After performing the "Scout" acquisition 310, the user is also given the ability to edit the reconstruction parameters 314, prior to performing the tomosynthesis acquisition 316. After performing the tomosynthesis acquisition 316, the images are processed 318.

Figure 4:
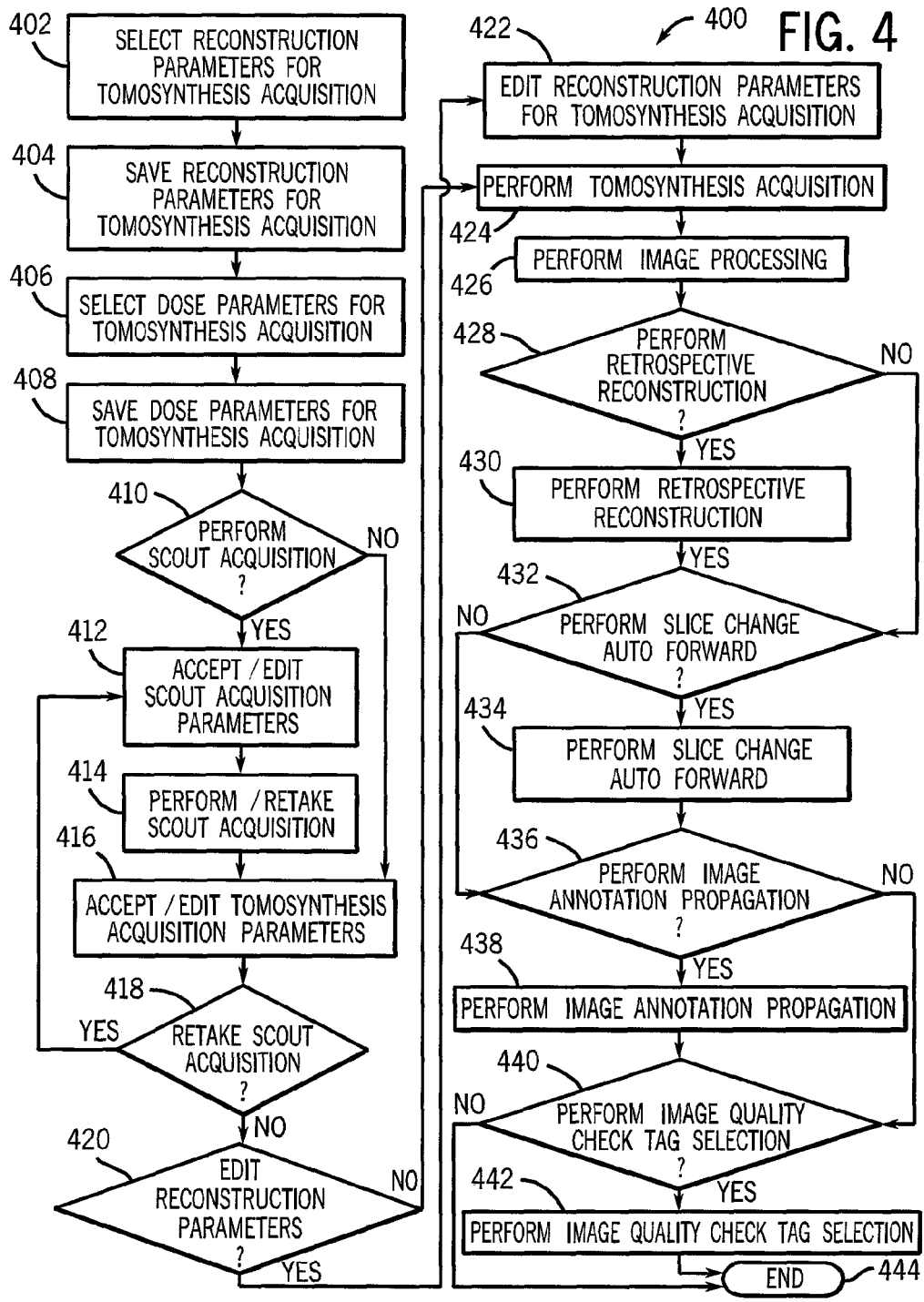
FIG. 4 is a flow diagram of an exemplary embodiment of a digital X-ray radiographic tomosynthesis system workflow method.

FIG. 4 is a flow diagram of an exemplary embodiment of a digital X-ray radiographic tomosynthesis system workflow method 400. This method 400 includes selecting reconstruction parameters prior to the start of an X-ray exposure for a tomosynthesis acquisition 402. These reconstruction parameters are saved by the tomosynthesis radiography system 404. The method 400 also includes selecting dose parameters prior to the start of an X-ray exposure for a tomosynthesis acquisition 406. These dose parameters are saved by the tomosynthesis radiography system 408. Prior to the start of a tomosynthesis acquisition, the user is given the opportunity to perform a "Scout" acquisition to obtain an optimal tomosynthesis exam 410. If the user elects to perform a "Scout" acquisition, the user is given the ability to accept or edit default "Scout" acquisition parameters 412, prior to performing the "Scout" acquisition 414. If the user elects not to perform a "Scout" acquisition, the user is given the ability to accept or edit default tomosynthesis acquisition parameters 416, prior to performing a tomosynthesis acquisition 424. After performing the "Scout" acquisition 414, the user is given the ability to accept or edit default tomosynthesis acquisition parameters 416, prior to performing the tomosynthesis acquisition 424. At this point, the user is given the ability to retake the "Scout" acquisition 418. If the user elects to retake the "Scout" acquisition, the user is given the ability to edit the "Scout" acquisition parameters 412, prior to retaking the "Scout" acquisition 414. If the user elects not to retake the "Scout" acquisition, the user is given the ability to edit the tomosynthesis reconstruction parameters 420, prior to performing a tomosynthesis acquisition 424. After retaking the "Scout" acquisition, the user is given the ability to edit the tomosynthesis acquisition parameters 416 and edit the tomosynthesis reconstruction parameters 420, prior to performing the tomosynthesis acquisition 424. If the user elects to edit the tomosynthesis reconstruction parameters, the user edits the tomosynthesis reconstruction parameters 422, prior to performing the tomosynthesis acquisition 424. If the user elects not to edit the tomosynthesis reconstruction parameters, the user performs the tomosynthesis acquisition 424. After performing the tomosynthesis acquisition 424, the images are processed 426. After the slice images are processed the user is given the ability to perform retrospective reconstruction 428. If the user elects to perform retrospective reconstruction, the user performs retrospective reconstruction 430. If the user elects not to perform retrospective reconstruction, the user is given the ability to perform slice change auto forward 432. If the user elects to perform slice change auto forward, the user performs slice change auto forward 434. If the user elects not to perform slice change auto forward, the user is given the ability to perform image annotation propagation 436. If the user elects to perform image annotation propagation, the user performs image annotation propagation 438. If the user elects not to perform image annotation propagation, the user is given the ability to perform image quality check tag selection 440. If the user elects to perform image quality check tag selection, the user performs image quality check tag selection 442 and the workflow method 400 is ended at step 444. If the user elects not to perform image quality check tag selection, the workflow method 400 ends at step 444.

Figure 5:
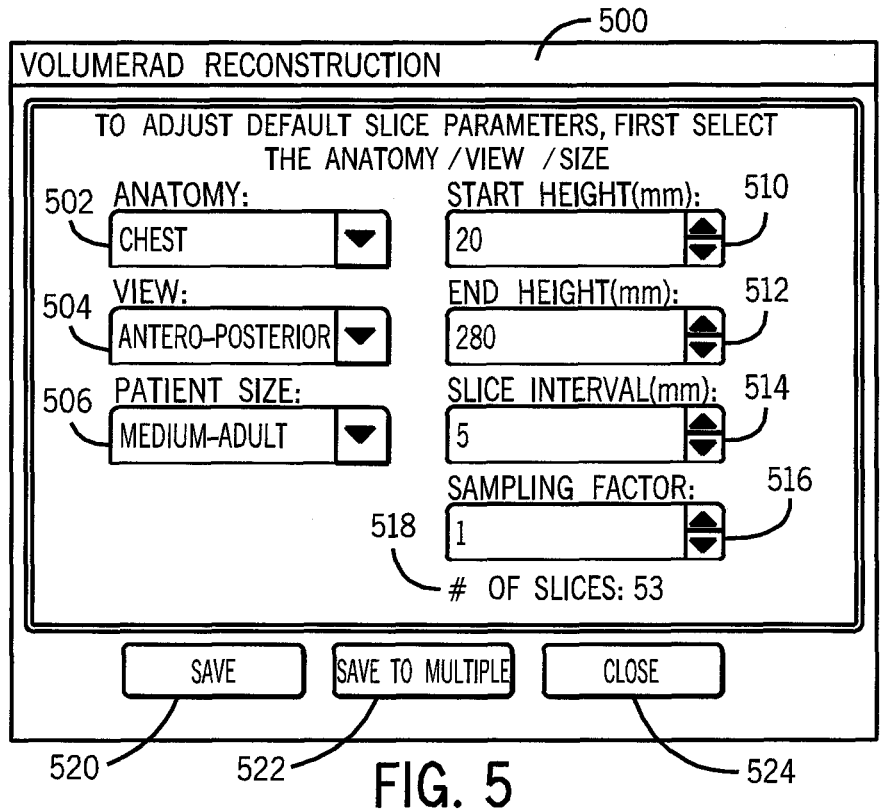
FIG. 5 is a schematic representation of an exemplary embodiment of a user interface tomosynthesis reconstruction preference edit tool.

FIG. 5 is a schematic representation of an exemplary embodiment of a user interface tomosynthesis reconstruction preference edit tool 500. This user interface tool 500 may be used for setting reconstruction preference parameters in a digital radiographic tomosynthesis system. The user interface tool 500 is a tomosynthesis preference edit tool that enables a user to customize slice reconstruction parameters for a specific anatomical view and patient size. When a system user is starting a tomosynthesis exam, they need to know: 1) where in the patient's anatomy should the slices be reconstructed; and 2) what dose should be used for the tomosynthesis acquisition (as compared to a single exposure acquisition). The user may also want to customize the system based on their previous knowledge and experiences. This is accomplished by using the tomosynthesis reconstruction preference user interface tool 500.

Reconstruction preferences define the slice parameters (start height, end height, slice interval, sampling factor) used to create the slices for a given anatomical view and patient size (anatomy, view, patient size). The user interface tool 500 enables a user to select or edit the slice reconstruction parameters for a tomosynthesis acquisition.

A user may select a specific anatomy 502, view 504, and patient size 506, and then select the reconstruction parameters (start height 510, end height 512, slice interval 514, sampling factor 516, # of slices 518) as described in Table 1.

TABLE 1

Tomosynthesis Reconstruction Parameters

| Function | Description |
|---|---|
| Start Height (mm) | Selects the distance from Tabletop or Wallstand surface at which the first slice is reconstructed. |
| End Height (mm) | Selects the distance from Tabletop or Wallstand surface at which the last slice is reconstructed. |
| Slice Interval (mm) | Selects the distance between reconstructed slices. |
| Sampling Factor | Selects the number of slices averaged for a thicker slice. |
| # of Slices | Displays the calculated number of slices based on the specified reconstruction parameters. |

Figure 6:
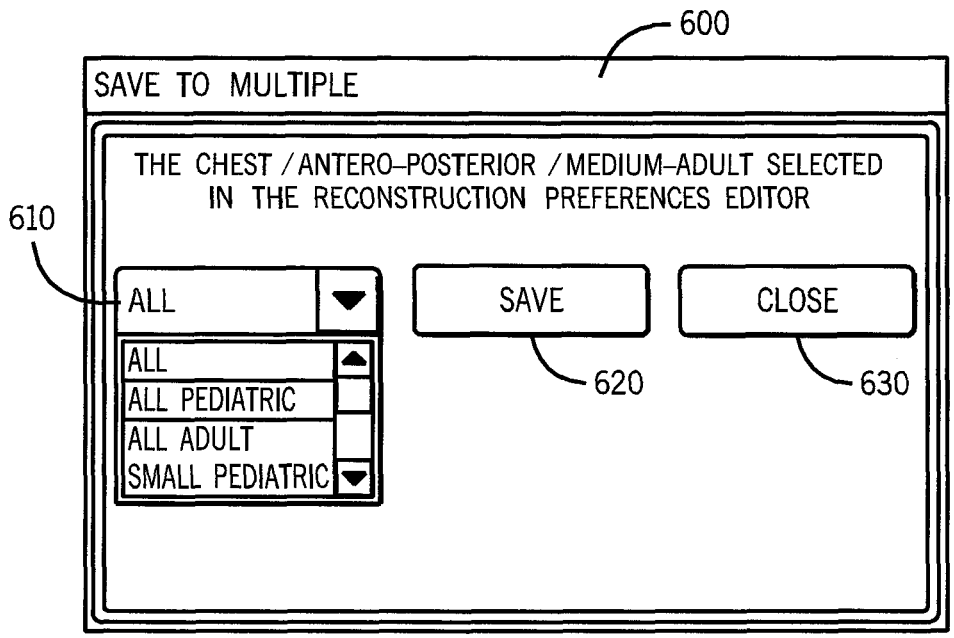
FIG. 6 is a schematic representation of an exemplary embodiment of a user interface "Save to Multiple" tool.

After selecting a set of reconstruction parameters, the user may select the "Save" function 520 to save the settings for the given anatomy, view and patient size into a database. The user interface tool 500 also may provide a "Save to Multiple" function 522 to save the same setting for other patient sizes. FIG. 6 illustrates a pop-up window user interface "Save To Multiple" tool 600 that appears upon selecting the "Save To Multiple" function 522 on the user interface tomosynthesis reconstruction preference edit tool 500 of FIG. 5. In FIG. 5, the "Save To Multiple" function 522 may save the settings of the user interface tomosynthesis reconstruction preference edit tool 500 to a specific patient size or to a different patient size. The "Close" function 524 may be to close the user interface tomosynthesis reconstruction preference edit tool 500 on the display.

In an exemplary embodiment, the anatomy 502 parameter may include a drop down list of various choices of anatomy. In an exemplary embodiment, the view 504 parameter may include a drop down list of various choices of views. In an exemplary embodiment, the patient size 506 parameter may include a drop down list of various choices of patient sizes, such as small adult, medium adult, large adult, small pediatric, medium pediatric, and large pediatric, for example.

In an exemplary embodiment, the reconstruction parameters may be predefined. In an exemplary embodiment, the start height 510 parameter may be any number specifying the starting point of the acquisition. In an exemplary embodiment, the end height 512 parameter may be any number specifying the ending point of the acquisition. In an exemplary embodiment, the slice interval 514 parameter may range from 1 mm to 50 mm. In an exemplary embodiment, the sampling factor 516 parameter may be any odd number up to the slice interval. The slice distance may be as low as 1 mm. The user interface tomosynthesis reconstruction preference edit tool 500 includes an indication of the expected number of slices 518 given currently selected parameter values 510, 512, 514, 516. The # of slices 518 parameter is a calculated value from the other reconstruction parameters defined above. In an exemplary embodiment, the reconstruction parameters (start height, end height, slice interval, sampling factor) may include default values for a given anatomical view and patient size (anatomy, view, patient size).

FIG. 6 is a schematic representation of an exemplary embodiment of a user interface "Save to Multiple" tool 600. This user interface tool 600 may be used to save the settings for the reconstruction parameters for a patient size group. This user interface tool 600 may also be used to save the settings for the reconstruction parameters for multiple exams (for example, intravenous pyelogram (IVP), abdomen, lower spine, etc). In other words, a user may save the settings in the user interface tomosynthesis reconstruction preference edit tool 500 for multiple exams.

The user interface "Save to Multiple" tool 600 may include a drop down list of various patient sizes 610, such as all, all pediatric, all adult, small pediatric, medium pediatric, large pediatric, small adult, medium adult, and large adult, for example. After selecting a patient size 610, the user may select a "Save" function 620 to save the settings for the selected patient size into a database. The "Close" function 630 may be used to close the user interface "Save to Multiple" tool 600 on the display.

Figure 7:
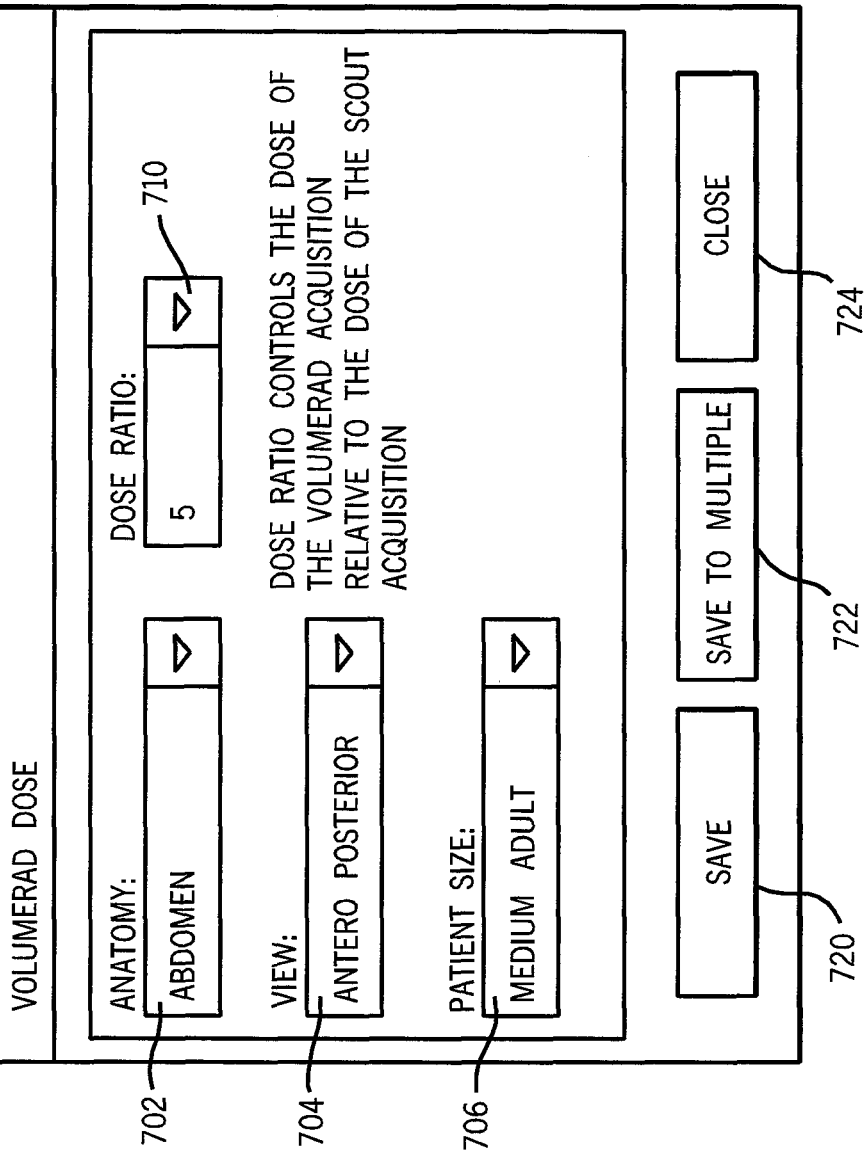
FIG. 7 is a schematic representation of an exemplary embodiment of a user interface dose preference edit tool.

FIG. 7 is a schematic representation of an exemplary embodiment of a user interface dose preference edit tool 700. This user interface tool 700 may be used for setting the dose in a digital radiographic tomosynthesis system. The user interface tool 700 enables a user to edit the dose ratio parameter for a tomosynthesis acquisition. The user interface tool 700 may be used to select a dose ratio 710 for a given anatomy 702, view 704, and patient size 706. The user interface tool 700 is a tomosynthesis preference edit tool that enables a user to customize dose parameters for a specific anatomical view and patient size.

The dose (or mAs) of a tomosynthesis acquisition is calculated based on the normal view single exposure acquisition that is called a "Scout" acquisition. For a tomosynthesis acquisition, typically, the same kVp may be as in the "Scout" image, but the mAs for each frame acquisition is derived from the mAs in the "Scout" acquisition:

$$mAs_{Tomo} = \frac{mAs_{scout} * DoseRatio}{N}$$

Where N is the total number of frames in a tomosynthesis sweep acquisition, and the DoseRatio is a multiplier that indicates how many times the total mAs in the tomosynthesis acquisition relative to the "Scout" acquisition.

A user may select a specific anatomy 702, view 704, and patient size 706, and then select the dose ratio 710. The dose ratio controls the dose of a tomosynthesis acquisition relative to the dose of the "Scout" acquisition.

In an exemplary embodiment, the user interface dose preference edit tool 700 enables a user to customize the dose ratio for a specific anatomical view and patient size, wherein the dose ratio controls the dose of a tomosynthesis acquisition relative to a Scout acquisition.

After selecting the dose ratio 710 parameter, the user may select the "Save" function 720 to save the dose ratio for the given anatomy, view and patient size into a database. The user interface tool 700 also may provide a "Save to Multiple" function 722 to save the same setting for other patient sizes. FIG. 6 illustrates a pop-up window user interface "Save To Multiple" tool 600 that appears upon selecting the "Save To Multiple" function 722 on the user interface dose preference edit tool 700. The "Save To Multiple" function 722 may save the dose ratio 710 setting of the user interface dose preference edit tool 700 to a specific patient size or to a different patient size. The "Close" function 724 may be to close the user interface dose preference edit tool 700 on the display.

In an exemplary embodiment, the anatomy 702 parameter may include a drop down list of various choices of anatomy. In an exemplary embodiment, the view 704 parameter may include a drop down list of various choices of views. In an exemplary embodiment, the patient size 706 parameter may include a drop down list of various choices of patient sizes, such as small adult, medium adult, large adult, small pediatric, medium pediatric, and large pediatric, for example.

In an exemplary embodiment, the dose parameter may be predefined. In an exemplary embodiment, the dose parameter (dose ratio) may include default values for a given anatomical view and patient size (anatomy, view, patient size).

Figure 8:
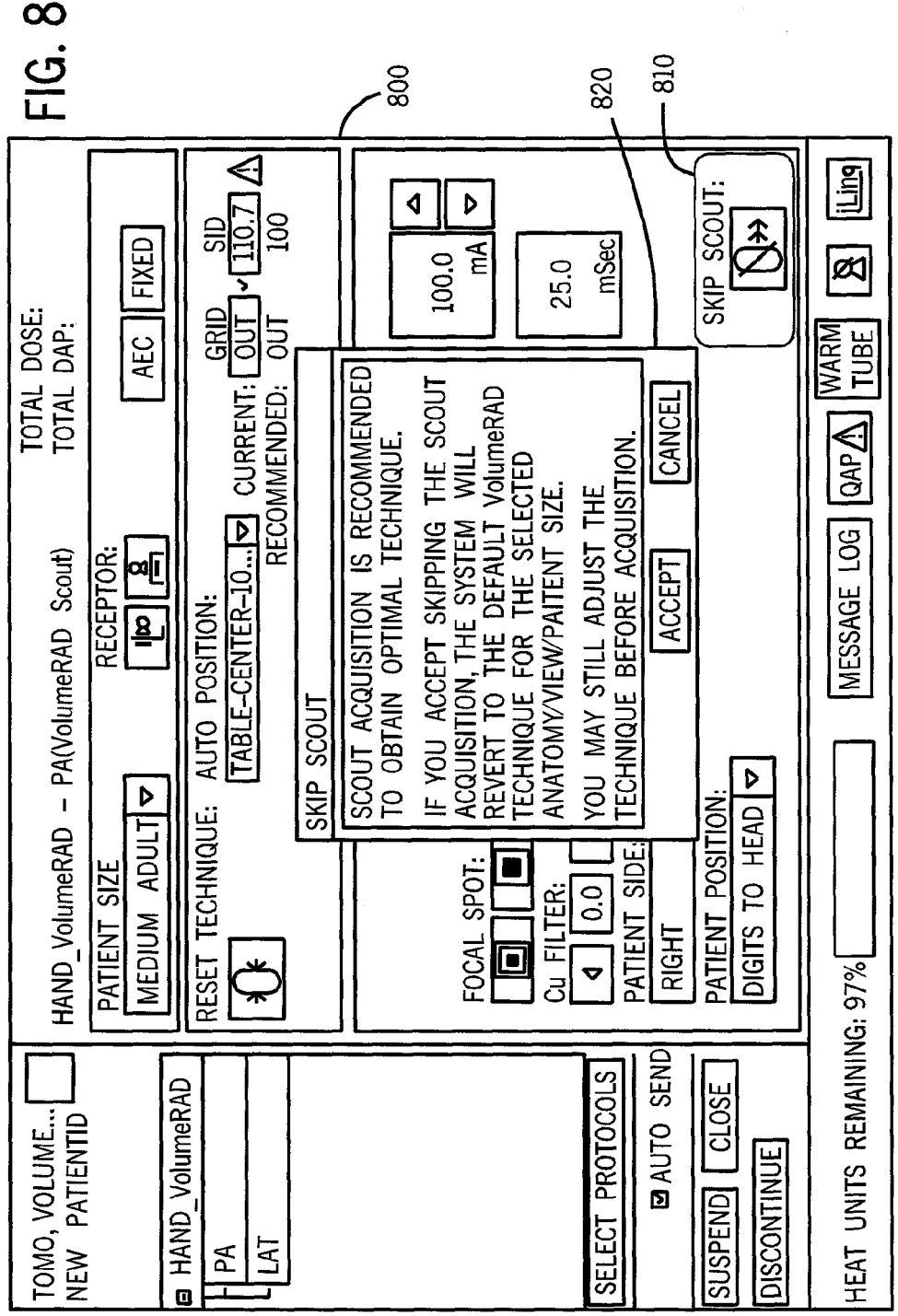
FIG. 8 is a schematic representation of an exemplary embodiment of a user interface "Scout" acquisition edit tool illustrating a "Skip Scout" function.

FIG. 8 is a schematic representation of an exemplary embodiment of a user interface "Scout" acquisition edit tool 800 illustrating a "Skip Scout" 810 function. This user interface tool 800 may be used for selecting "Scout" acquisition parameters and performing a "Scout" acquisition in a digital radiographic tomosynthesis system. The user interface tool 800 is a "Scout" acquisition edit tool for customizing "Scout" acquisition parameters. Whenever a tomosynthesis acquisition is started, the system will start at a tomosynthesis "Scout" acquisition user interface tool 800. The "Scout" acquisition is a standard, conventional single exposure acquisition, which may be to determine the patient position and exposure settings, such as field of view (FOV), and X-ray techniques (kV, mAs). Once the X-ray exposure is finished, the user may confirm that the parameter settings are correct. Multiple "Scout" acquisitions may be taken to ensure that the sweep acquisition is correct.

However, the "Scout" acquisition may increase exam time and dose to a patient. In order to reduce the dose and exam time, a "Skip Scout" 810 function may be available on the user interface "Scout" acquisition edit tool 800 for advanced users. Selecting the "Skip Scout" 810 function causes a confirmation pop-up window 820 to appear on the user interface "Scout" acquisition edit tool 800 that may read something like: "Scout acquisition is recommended to obtain optimal technique. If you ACCEPT skipping the "Scout" acquisition, the system will revert to the DEFAULT VolumeRAD technique for the selected Anatomy/View/Patient Size. You may still adjust the technique before acquisition." Accepting the "Skip Scout" function will automatically switch the system to a user interface tomosynthesis acquisition edit tool without completing a "Scout" acquisition.

FIG. 9 is a schematic representation of an exemplary embodiment of a user interface tomosynthesis acquisition edit tool 900 illustrating a "Retake Scout" 910 function. This user interface tool 900 may be used for selecting tomosynthesis acquisition parameters and performing a tomosynthesis acquisition in a digital radiographic tomosynthesis system. The user interface tool 900 is a tomosynthesis acquisition edit tool for customizing tomosynthesis acquisition parameters. After a conventional single exposure "Scout" acquisition is completed or the "Skip Scout" function is selected, the system automatically switches to a tomosynthesis acquisition mode. This user interface tool 900 may include tomosynthesis acquisition information 920. In an exemplary embodiment, the user interface tomosynthesis acquisition edit tool 900 displays the number of exposures to be acquired (acquisitions), the number of slices to be displayed at the end of a tomosynthesis acquisition, and the total acquisition time 920. In an exemplary embodiment, the user interface tomosynthesis acquisition edit tool 900 displays acquisition dose information after the completion of a tomosynthesis acquisition. In addition, the user interface tool 900 may include an operation instruction message 930. For example, the operation instruction message may include information regarding performing auto-positioning to move the X-ray source into an initial position for a tomosynthesis acquisition. While in the tomosynthesis acquisition mode, the user interface tomosynthesis acquisition edit tool 900 may include a "Retake Scout" 910 function that takes the system back to the "Scout" acquisition mode and the user interface "Scout" acquisition edit tool 800 illustrated in FIG. 8.

Figure 10:
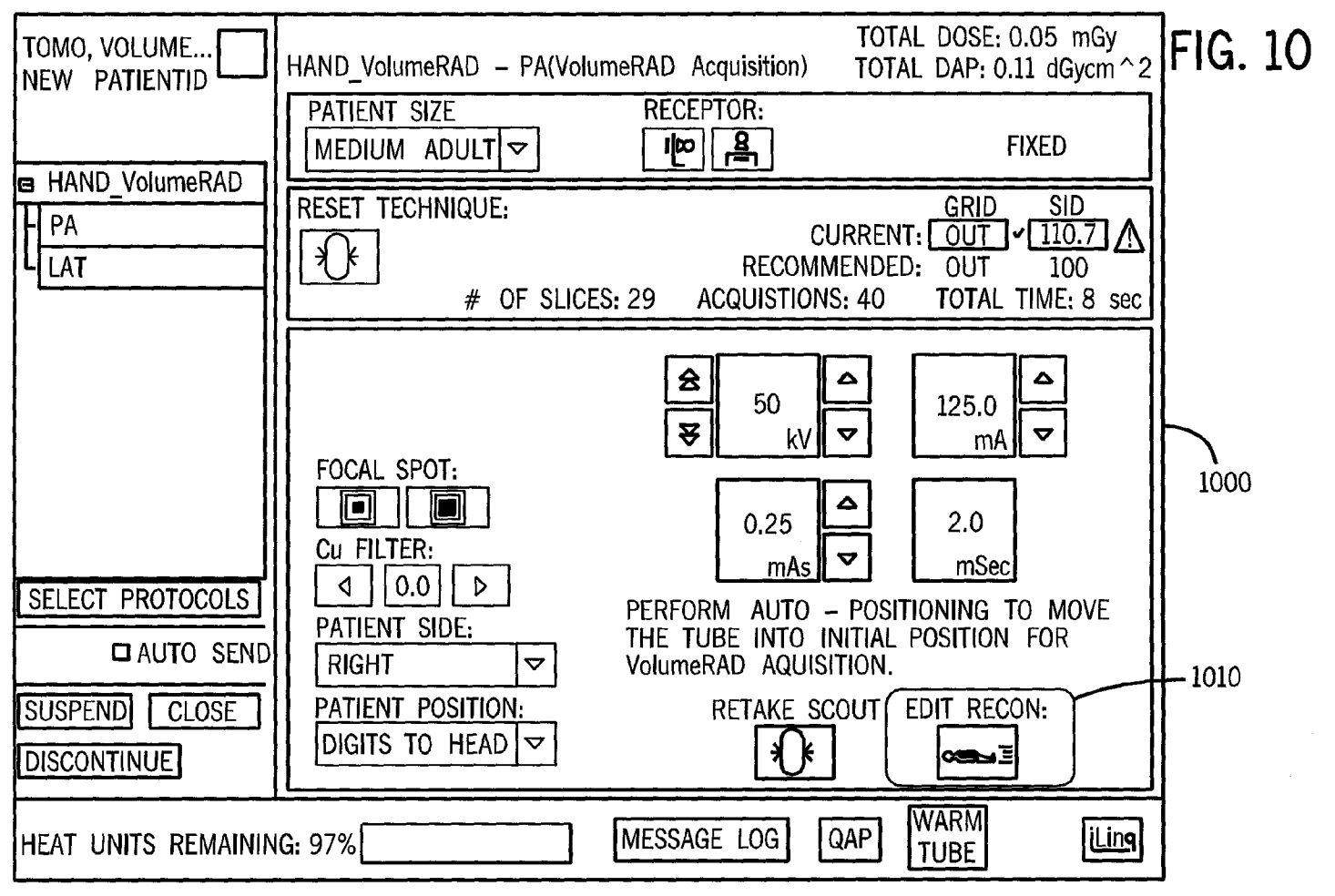

FIG. 10 is a schematic representation of an exemplary embodiment of a user interface tomosynthesis acquisition edit tool 1000 illustrating an "Edit Recon" (edit reconstruction) 1010 function. This user interface tool 1000 may be used for editing tomosynthesis reconstruction parameters prior to performing a tomosynthesis acquisition. The user interface tool 1000 is a tomosynthesis acquisition edit tool for customizing tomosynthesis acquisition parameters. Upon selecting the "Edit Recon" 1010 function, a pop-up window user interface "Edit Recon" (edit reconstruction) tool 1100 shown in FIG. 11 appears, which allows a user to review and/or change the reconstruction parameters for the current acquisition without changing the default parameters for the given exam type.

Figure 11:
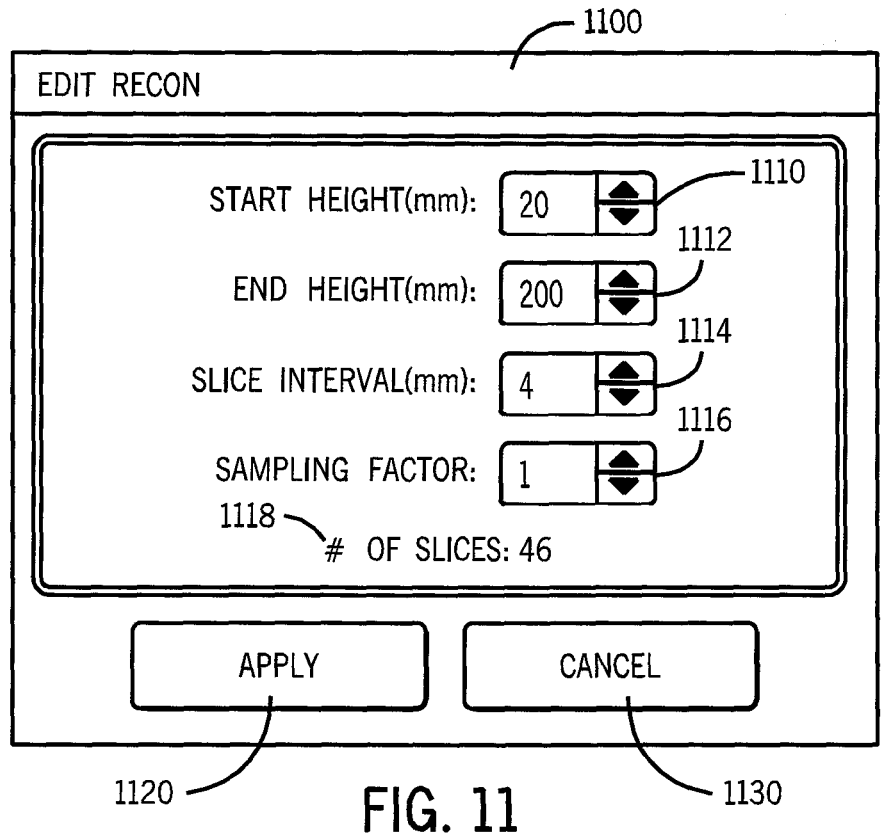
FIG. 11 is a schematic representation of an exemplary embodiment of a user interface "Edit Recon" (edit reconstruction) tool.

FIG. 11 is a schematic representation of an exemplary embodiment of a user interface "Edit Recon" (edit reconstruction) tool 1100 illustrating the tomosynthesis reconstruction parameters. This user interface tool 1100 may be used for editing tomosynthesis reconstruction parameters prior to performing a tomosynthesis acquisition. The tomosynthesis reconstruction parameters may include start height 1110, end height 1112, slice interval 1114, sampling factor 1116, and # of slices 1118. The "Apply" function 1120 may be used to save the current settings of the tomosynthesis reconstruction parameters, but may not change the default settings. The "Cancel" function 1130 may be used to cancel the current settings of the tomosynthesis reconstruction parameters.

Figure 12:
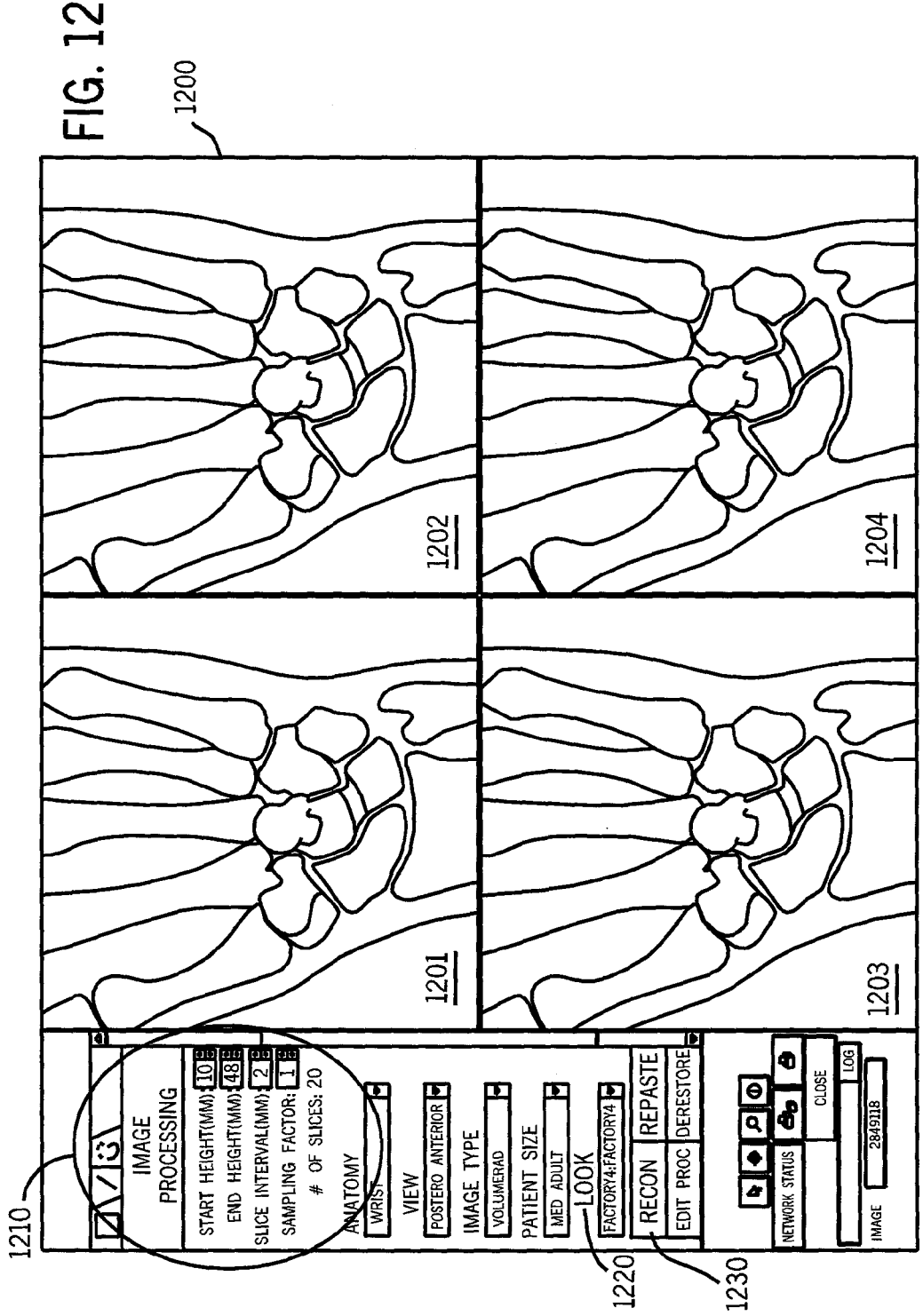
FIG. 12 is a schematic representation of an exemplary embodiment of a user interface "Retro Recon Image Processing" (retrospective reconstruction image processing) edit tool.

FIG. 12 is a schematic representation of an exemplary embodiment of a user interface "Retro Recon Image Processing" (retrospective reconstruction image processing) edit tool 1200. This user interface tool 1200 includes a plurality of slice images 1201, 1202, 1203, 1204. This user interface tool 1200 is a slice image processing edit tool that may be used for changing tomosynthesis reconstruction parameters of slice images after performing a tomosynthesis acquisition. The user interface tool 1200 is a retrospective reconstruction edit tool that enables a user to customize slice reconstruction parameters of slice images after performing a tomosynthesis acquisition. In other words, the user interface tool 1200 is a retrospective reconstruction edit tool that enables a user to easily and intuitively reconstruct tomosynthesis slices with different parameters retrospectively, that is after the images have been acquired and displayed with default parameters.

A retrospective reconstruction may be used to reconstruct the slice images after a tomosynthesis acquisition is performed. The user may select different tomosynthesis reconstruction parameters 1210 and different image processing "Looks" 1220 to reconstruct a new set(s) of slice images. The reconstruction parameters 1210 (start height, end height, slice interval, sampling factor, # of slices) in the user interface 1200 are defined in Table 1. All that a user needs to do is to select a set of reconstruction parameters 1210 and a predefined factory "Look" 1220, then select the "Recon" 1230 function to start the retrospective reconstruction. After the images are acquired, a user may select the same projection data to perform a different reconstruction. In other words, after a tomosynthesis acquisition, a user may select different reconstruction parameters 1210 and a different image processing "Look" 1220 to reconstruct a new set(s) of slice images.

In an exemplary embodiment, the user interface retrospective reconstruction image processing edit tool 1200 enables a user to reconstruct tomosynthesis slices with different parameters retrospectively, that is after the images have been acquired and displayed with default parameters.

Figure 13:
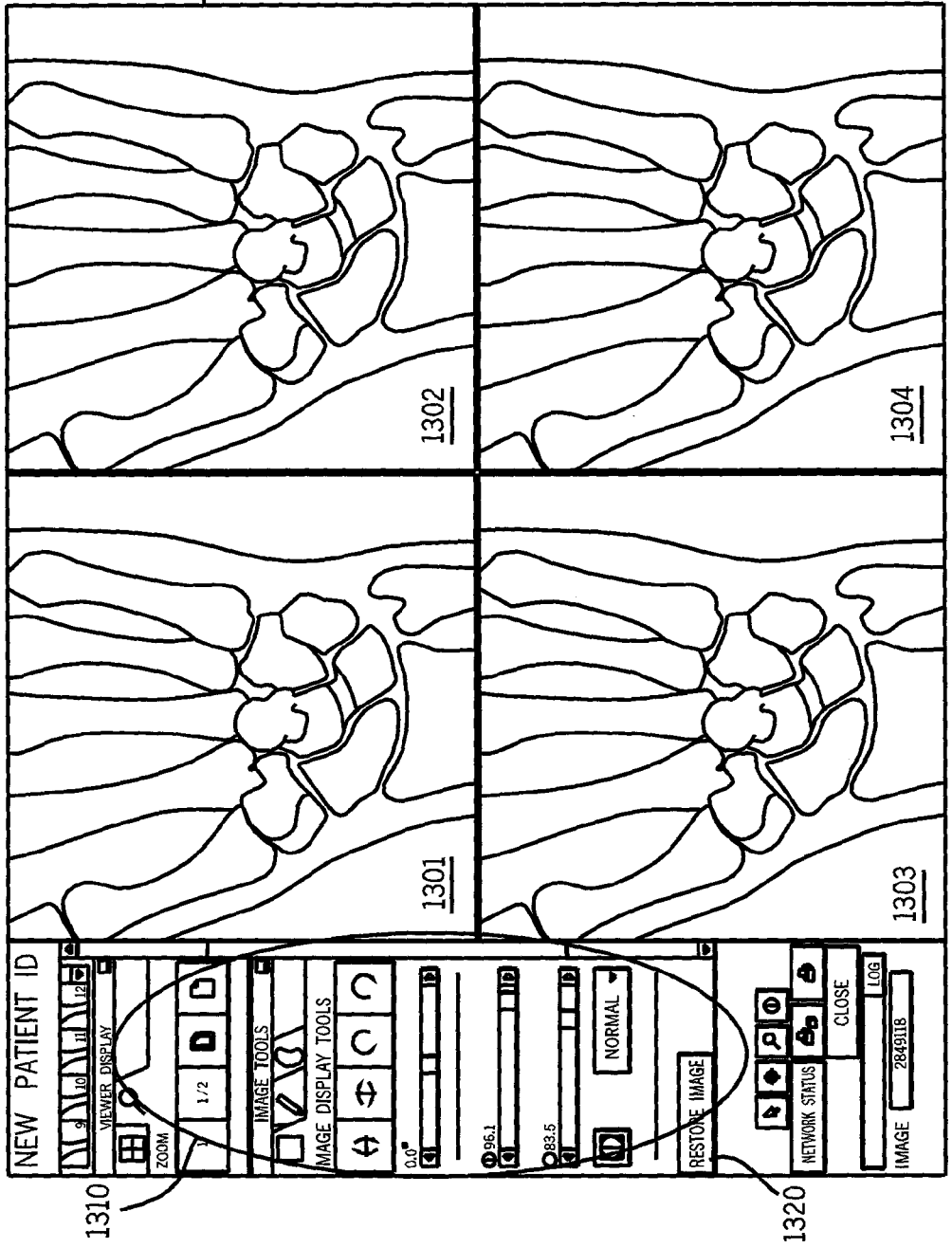
FIG. 13 is a schematic representation of an exemplary embodiment of a user interface "Slice Change Auto Forward" tool.

FIG. 13 is a schematic representation of an exemplary embodiment of a user interface "Slice Change Auto Forward"

tool 1300. This user interface tool 1300 includes a plurality of slice images 1301, 1302, 1303, 1304. This user interface tool 1300 is a slice image processing edit tool that may be used for changing image presentation parameters of slice images after performing a tomosynthesis acquisition. In other words, the user interface tool 1300 is an auto-forward tool that enables a user to apply changes to an entire tomosynthesis image slice series when any single slice's parameters have been changed.

Because tomosynthesis slice images show the same anatomical structures at different heights, it may be convenient to allow a user review the slice images with the same image presentation parameters, such that when one of the slice images is changed, the change is automatically forwarded to all of the slice images in a series of slice images. A plurality of image display tools 1310 are provided on the user interface tool 1300 for allowing a user to change the image presentation parameters of the slice images. In an exemplary embodiment, some of the image presentation parameters that may be changed include window width (WW), window level (WL), image invert, rotation, flip, zoom, and values of interest look-up table (VOI LUT) selection, for example. A "Restore Image" 1320 function may also be available on the user interface tool 1300 to restore the slice images to their original or previous presentations using the original or previous image presentation parameters.

In an exemplary embodiment, the user interface "Slice Change Auto Forward" tool 1300 enables a user to apply changes to an entire tomosynthesis image slice series when any single slice's attributes have been changed. In an exemplary embodiment, the user interface "Slice Change Auto Forward" tool 1300 enables a user to change the display brightness and contrast of an entire tomosynthesis image slice series. In an exemplary embodiment, the user interface "Slice Change Auto Forward" tool 1300 enables a user to change the display zoom factor of an entire tomosynthesis image slice series. In an exemplary embodiment, the user interface "Slice Change Auto Forward" tool 1300 enables a user to change the image display orientation of an entire tomosynthesis image slice series.

FIG. 14 is a schematic representation of an exemplary embodiment of a user interface "Image Annotation Propagation" tool 1400. This user interface tool 1400 includes a plurality of slice images 1401, 1402, 1403, 1404. This user interface tool 1400 is a slice image processing edit tool that may be used for adding or removing annotations to the slice images after performing a tomosynthesis acquisition. In other words, the user interface tool 1400 is an annotation tool that enables a user to add or remove annotations to an entire tomosynthesis image slice series or a range of slice images in a series.

Because tomosynthesis slice images show the same anatomical structures at different heights, it may be desirable to allow a user to add annotations to all or selected slice images in a series of slice images. These annotations may be added to a selected slice, a range of slices, or all slices in a series of slice images. A plurality of image annotation tools 1410 are provided on the user interface tool 1400 for allowing a user to add annotations to the slice images. In an exemplary embodiment, some of the annotations that may be added include line, ellipse, cobb, text string, "Hide", "Erase", "Erase All", and "RL", for example. The "RL" annotation may be added to show the "Right" or "Left" of anatomy. Examples of annotations 1411, 1412, 1413, 1414 added to slice images 1401, 1402, 1403, 1404, respectively, are shown in FIG. 14. An "Apply to Slices" 1420 function may be available on the user interface tool 1400 to add annotations to selected slice images. Therefore, when a user desires to add annotations to selected slice images, the user can add the annotations by selecting the "Apply to Slices" 1420 function. In an exemplary embodiment, the annotations may be automatically added to all slices in a series of slice images.

In an exemplary embodiment, the user interface "Image Annotation Propagation" tool 1400 enables a user to add or remove an annotation to an entire tomosynthesis image slice series or a range of slices in a series. In an exemplary embodiment, the user interface "Image Annotation Propagation" tool 1400 enables a user to change the location of an annotation in an entire tomosynthesis image slice series or a range of slices in a series.

Figure 15:
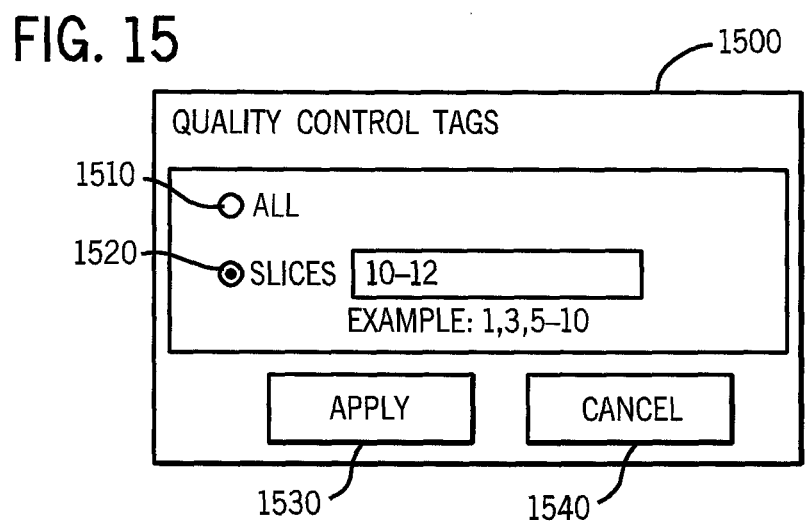
FIG. 15 is a schematic representation of an exemplary embodiment of a user interface "Quality Control Tags" selection tool.

FIG. 15 is a schematic representation of an exemplary embodiment of a user interface "Quality Control Tags" selection tool 1500. This user interface tool 1500 may be used for adding "Quality Control Tags" to all or selected slice images is a series of slice images after performing a tomosynthesis acquisition. A quality control tag is applied to a slice image if it is validated as an acceptable image. Since a large number of slice images are generated in a tomosynthesis acquisition, it is necessary for a user to select all 1510 of the slice images in a series or a range 1520 of slice images in a series for application of quality control tags on the selected slice images. Therefore, quality control tags may be applied to all 1510 of the slice images, or a specific range of slice images 1520 that may include specific slices or a range of slices. The "Apply" function 1530 may be used to apply quality control tags to the selected slice images. The "Cancel" function 1540 may be used to cancel the current application of quality control tags to the selected slice images.

In an exemplary embodiment, "Auto Push" and "Auto Print" functions are options to automatically send "good" images to a picture archiving and communication system (PACS) or a printer so a radiologist or other medical professional can review them. In an exemplary embodiment, the system may be configured for an "Auto Tag (Quality Check)" on or off to automatically apply (on) or don't apply (off) quality control tags to slice images.

FIG. 16 is a schematic representation of an exemplary embodiment of a user interface "Image Viewer Show Slices Tagged" tool 1600. This user interface tool 1600 includes a plurality of slice images 1601, 1602, 1603, 1604. This user interface tool 1600 is a slice image processing edit tool that may be used for adding "Quality Control Tags" to all or selected slice images is a series of slice images. In other words, the user interface tool 1600 is a quality check tag tool that enables a user to add or remove quality check tags to and from an entire tomosynthesis image slice series or a range of slices in a series.

A "Quality Control Tags" 1610 function is provided in the user interface tool 1600 for allowing a user to apply quality control tags to selected image slices. A user may select all 1510 of the slices or a range 1520 of slices to be tagged through the user interface tool 1500 shown in FIG. 15. When a range of slices is tagged, a quality control tag marker "T" is displayed in each image slice's right bottom corner. For example, FIG. 16 shows three slice images 1602, 1603, 1604 that are quality control tagged with a quality control tag marker "T" displayed in each image slice's right bottom corner, and one slice image 1601 that is not quality control tagged. The quality control tagged images 1602, 1603, 1604 may be sent to a PACS, a printer, or a radiologist or other medical professional for review.

In an exemplary embodiment, the user interface "Image Viewer Show Slices Tagged" tool 1600 enables a user to add or remove a quality check tag to an entire tomosynthesis image slice series or a range of slices in a series.

In an exemplary embodiment, the user interface tools disclosed may be implemented in a digital X-ray radiographic tomosynthesis system. In an exemplary embodiment, the user interface tools disclosed may be implemented in a digital X-ray mammography tomosynthesis system.

The embodiments described provide user-friendly interfaces and workflows for efficient clinical use of a digital X-ray radiographic tomosynthesis system. The user-friendly interfaces and workflows are configured to help a user easily set tomosynthesis reconstruction, dose, and acquisition parameters, and customize them for different exams, and/or patient groups. In addition, the user-friendly interfaces and workflows enable a user to readily adjust tomosynthesis reconstruction, dose, and acquisition parameters in an intuitive manner.

Several embodiments are described above with reference to drawings. These drawings illustrate certain details of specific embodiments that implement systems, methods and computer programs. However, the drawings should not be construed as imposing any limitations associated with features shown in the drawings. This disclosure contemplates methods, systems and program products on any machine-readable media for accomplishing its operations. As noted above, the embodiments of the may be implemented using an existing computer processor, or by a special purpose computer processor incorporated for this or another purpose or by a hardwired or wireless system.

Embodiments are described in the general context of method steps which may be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As noted above, embodiments within the scope of the included program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions thereof might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

Those skilled in the art will appreciate that the embodiments disclosed herein may be applied to the formation of any radiography system. Certain features and elements of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

What is claimed is:

1. A tomosynthesis system comprising:
a user interface providing a tomosynthesis reconstruction preference edit tool enabling a user to select specific anatomy, view and patient size, and select slice reconstruction parameters including start and end height, slice interval, and sampling factor for the selected specific anatomy, view and patient size;
wherein the sampling factor is defined as a slice reconstruction parameter for selection of a number of image slices averaged for a thicker slice; and a dose preference edit tool enabling a user to select an imaging dose ratio for a specific anatomy, view and patient size for a tomosynthesis acquisition;

wherein the imaging dose ratio controls the dose of a tomosynthesis acquisition relative to a Scout acquisition.

2. The tomosynthesis system of claim 1, wherein the tomosynthesis preference edit tool includes an indication of the expected number of slices, given currently selected slice reconstruction parameters.

3. The tomosynthesis system of claim 1, wherein the tomosynthesis preference edit tool includes a save function for saving slice reconstruction parameters for the selected specific anatomy, view and patient size into a database, and a save to multiple function for saving slice reconstruction parameters for a specific patient size group or a different patient size into the database.

4. The tomosynthesis system of claim 1, wherein the imaging dose preference edit tool includes a save function for saving the imaging dose ratio for the selected specific anatomy, view and patient size into a database, and a save to multiple function for saving the imaging dose ratio for a specific patient size group or a different patient size.

5. The tomosynthesis system of claim 1, further comprising the user interface providing a retrospective reconstruction image processing edit tool enabling the user to reconstruct tomosynthesis slices with different slice reconstruction parameters after the tomosynthesis acquisition.

6. The tomosynthesis system of claim 1, further comprising the user interface providing a slice image change auto forward edit tool enabling the user to apply image presentation parameter changes to an entire tomosynthesis image slice series when any single slice's image presentation parameters have been changed.

7. The tomosynthesis system of claim 6, wherein the slice image change auto forward edit tool enables the user to change a display brightness and contrast of the entire tomosynthesis image slice series.

8. The tomosynthesis system of claim 6, wherein the slice image change auto forward edit tool enables the user to change a display zoom factor of the entire tomosynthesis image slice series.

9. The tomosynthesis system of claim 6, wherein the slice image change auto forward edit tool enables the user to change an image display orientation of the entire tomosynthesis image slice series.

10. The tomosynthesis system of claim 1, further comprising the user interface providing an image annotation propagation edit tool enabling the user to add or remove an annotation to an entire tomosynthesis image slice series or a range of tomosynthesis image slices in a tomosynthesis image slice series.

11. The tomosynthesis system of claim 10, wherein the image annotation propagation edit tool enables the user to change a location of the annotation in the entire tomosynthesis image slice series or the range of tomosynthesis image slices in the tomosynthesis image slice series.

12. The tomosynthesis system of claim 10, wherein the image annotation propagation edit tool includes a quality control tag selection function enabling the user to add or remove a quality check tag to the entire tomosynthesis image slice series or the range of tomosynthesis image slices in the tomosynthesis image slice series.

13. The tomosynthesis system of claim 1, further comprising the user interface providing a scout acquisition edit tool enabling the user to select scout acquisition parameters for a single exposure scout acquisition to determine patient position and exposure settings.

14. The tomosynthesis system of claim 13, wherein the scout acquisition edit tool includes a skip scout function enabling the user to skip the single exposure scout acquisition.

15. The tomosynthesis system of claim 1, further comprising the user interface providing a tomosynthesis acquisition edit tool enabling the user to select tomosynthesis acquisition parameters for a multiple exposure tomosynthesis acquisition.

16. The tomosynthesis system of claim 15, wherein the tomosynthesis acquisition edit tool includes a retake scout function enabling the user to retake the scout acquisition.

17. The tomosynthesis system of claim 15, wherein the tomosynthesis acquisition edit tool includes an edit reconstruction function enabling the user to edit the slice reconstruction parameters.

* * * * *